US009492177B2

(12) United States Patent
Saunders et al.

(10) Patent No.: US 9,492,177 B2
(45) Date of Patent: Nov. 15, 2016

(54) JUNCTIONAL TOURNIQUET

(71) Applicants: North American Rescue, LLC, Greer, SC (US); BOARD OF REGENTS OF THE UNIVERSITY OF TEXAS SYSTEM, Austin, TX (US)

(72) Inventors: Darrel Saunders, Simpsonville, SC (US); Ricardo Flores-Artola, Simpsonville, SC (US); Joanne Walters, Blue Ridge, GA (US); Michael Duncan, Greer, SC (US); Lester Martinez-Lopez, Valrico, FL (US); Joshua Markham, Milford, OH (US); Brent Bronson, Duncan, SC (US); John B. Holcomb, Austin, TX (US); Keith Gates, Austin, TX (US); Andy Burgess, Austin, TX (US)

(73) Assignees: North American Rescue, LLC, Greer, SC (US); The University Of Texas Health Care Center at Houston, Houston, TX (US)

( * ) Notice: Subject to any disclaimer, the term of this patent is extended or adjusted under 35 U.S.C. 154(b) by 648 days.

(21) Appl. No.: 13/801,462

(22) Filed: May 14, 2013

(65) Prior Publication Data

US 2013/0296921 A1  Nov. 7, 2013

(51) Int. Cl.
*A61B 17/00* (2006.01)
*A61B 17/132* (2006.01)

(52) U.S. Cl.
CPC ........ *A61B 17/1325* (2013.01); *A61B 17/1327* (2013.01)

(58) Field of Classification Search
CPC ............ A61B 17/132; A61B 17/1322; A61B 17/1325; A61B 17/1327
See application file for complete search history.

(56) References Cited

U.S. PATENT DOCUMENTS 5,139,512 A * 8/1992 Dreiling .................... A61F 5/32
606/201

* cited by examiner

*Primary Examiner* — Ashley Fishback
(74) *Attorney, Agent, or Firm* — McNair Law Firm, P.A.; Douglas W. Kim (57) ABSTRACT

The present invention is a tourniquet comprising: a strap; a pelvic pad included in the strap having a pocket defined in the pelvic pad for receiving a semi-rigid stiffening member; base plates slidably attached to the strap allowing the base plates to be positioned along the strap; a threaded shaft received in each of the base plates; a pressure pad removable attached to a distal end of each of the shafts; a handle attached to a proximal end of each of the shafts having openings defined in each end of the handle; and, a rotational arresting strap attached to each base plate having a securing tab that can be received in one of the handle openings thereby preventing the shaft from rotating when the securing tab is received in sand handle opening.

18 Claims, 7 Drawing Sheets

FIG. 8

JUNCTIONAL TOURNIQUET

CLAIM OF PRIORITY

This patent application claims priority on U.S. Patent Provisional Application Ser. No. 61/625,729 filed Apr. 18, 2012.

FIELD OF THE INVENTION

This invention is directed to a tourniquet designed to apply pressure to wounds located in the junction between the trunk and thigh and more specifically, to a tourniquet having the ability to apply pressure circumferentially with discrete pressure points in the trunk/thigh junction.

BACKGROUND OF THE INVENTION

Hemorrhage is one of the most common causes of preventable combat death in modern warfare. In response, efforts to create new and more effective and useful battlefield tourniquets has increased. For example, U.S. Pat. No. 4,469,099 is a Pneumatic Tourniquet described as a pneumatic tourniquet having an inflatable cuff, a pressurizing mechanism for pressurizing the cuff, a pressure relief mechanism for depressurizing the cuff, a pressure sensing mechanism for sensing the pressure to which the cuff is pressurized and a pressure regulator mechanism for selectably activating the pressurizing mechanism and the pressure relief means to maintain the cuff pressure near a selected pressure. Visual and audible alarm signals are triggered if the cuff pressure exceeds a cuff pressurization limit, if the cuff pressure falls below a cuff depressurization limit, or if the cuff has remained pressurized for, or in excess of a selected time period. A computer may be used to sense the cuff pressure and pressurized or depressurized the cuff as required to maintain the cuff pressure within upper and lower cuff pressure limits. However, this device is ill suited for wounds in the trunk/thigh junction as it does not have the ability to apply pressure to the junctional area.

U.S. Pat. No. 7,892,253 (the C-A-T tourniquet) is also an ill equipped tourniquet for applying pressure to a junctional wound. Specifically, this reference is designed for use when pressure is applied circumferentially. United States Patent Application 2010/0152770 describes a bleed out prevention system and method including an adjustable length attachment belt assembly which is passed around the body of a human being suspected of having an injured or severed major blood vessel where the adjustable length attachment belt assembly positions a plunger plate assembly over a location where compressive force can be applied to a portion of the major blood vessel which has not been injured or severed. However, this design is difficult to apply to a fallen patient, can only apply pressure to a single wound location, has several removable parts that can be lost in shipping, storage or use, includes straps that are prone to slipping out of place, does not have the ability to prevent the pressure points from loosening and does not allow pressure points to be modifiably positioning for differing body types and wound locations.

With body armor, there is a "weakness" where the body armor does not cover the junctional region and, therefore, wounds in this area have become more common. In fact, some studies report that with devices such as the C-A-T and the increased use of body armor, junctional wounds are now more likely to cause preventable combat death than wounds localized to limbs (including the complete loss of a limb). In fact, the Committee on Tactical Combat Casualty Care recently made junctional (truncal) tourniquets a research priority. This is particularly true given the fact that the Iliac and femoral artery as located in the junction between the leg and torso.

Accordingly, an object of the present invention is to provide a junctional tourniquet that can be easily packaged and stored while allowing pressure to be applied to a plurality of wound sites.

It is another object of the present invention to have pressure pads that can be positioned along the strap to as needed cased upon the injured individual body type and wound location.

SUMMARY OF THE INVENTION

The above objectives are accomplished by providing a tourniquet for use at junction points of an injured individual comprising: a strap for releasably encircling an injured individual; a pelvic pad included in the strap having a pocket defined in the pelvic pad for receiving a semi-rigid stiffening member; a plurality of base plates slidably attached to the strap allowing the base plates to be positioned along the strap; a shaft opening defined in each base plate having threads on an interior surface of the shaft openings; a threaded shaft received in each of the base plates; a pressure pad removable attached to a distal end of each of the shafts; a handle attached to a proximal end of each of the shafts having openings defined in each end of the handle; and, a rotational arresting strap attached to each base plate having a securing tab that can be received in one of the handle openings thereby preventing the shaft from rotating when the securing tab is received in sand handle opening.

The pressure pad can includes a trapezoidal cross section that reduces in area from the rear of the pressure pad to the front of the pressure pad. In one embodiment, the pressure pad includes a rear end having a rear width and a front end having a front width wherein the front width and the rear width have a ratio of about 2:1. The side of the pressure pad can have a side width wherein the ratio of the first end and the side width is about 2.25:1. The pressure pad can include a contact surface having an area of between 35 cm and 45 cm.

Rotational arresting straps can be included that are slidably attached to the base plates so that the rotational arresting straps can be tensioned to arrest rotational movement of the shafts. A slide lock carried by each rotational arresting strap preventing the rotational arresting straps from losing tension can be included.

A friction member can be attached to the base plate for engaging a friction opening in the pressure pad further restriction the ability to of the pressure pad to rotate relative to the base plate. A rigid core can be internal to the pressure pads having an opening for receiving the threaded shaft. The pressure pads can be rotatably press fit to the shafts allowing the pressure pad to rotate about the shaft. A tightening buckle at the ends of the strap can be included allowing the strap to be secured around the pelvic region of the injured individual placing tension on the pelvic region of the injured individual.

DESCRIPTION OF THE DRAWINGS

The construction designed to carry out the invention will hereinafter be described, together with other features thereof. The invention will be more readily understood from a reading of the following specification and by reference to the accompanying drawings forming a part thereof, wherein an example of the invention is shown and wherein.

DESCRIPTION OF A PREFERRED EMBODIMENT

Figure 1:
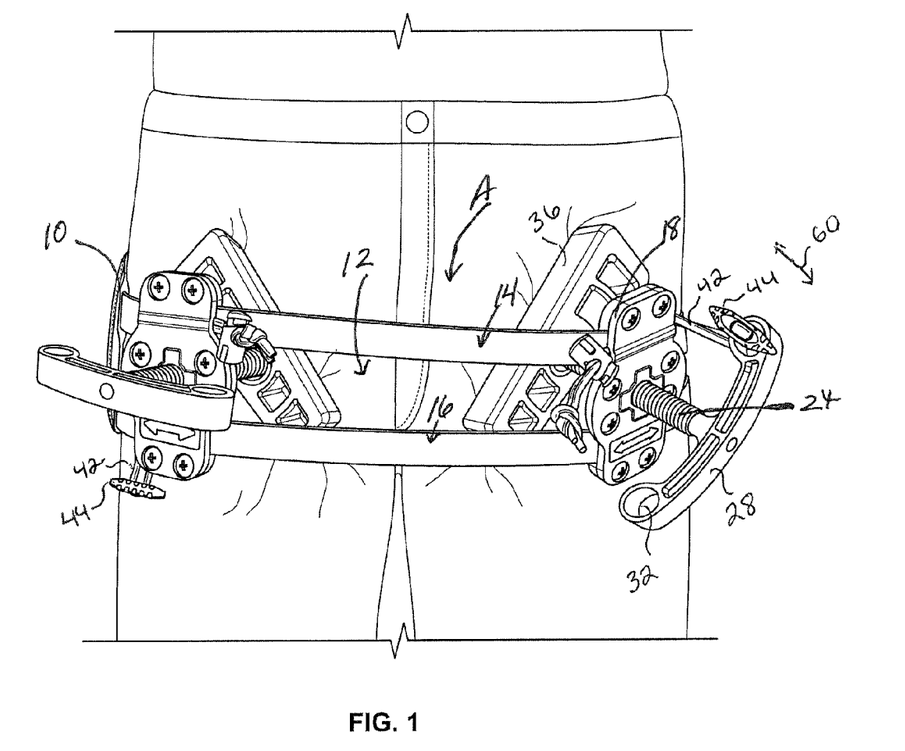
FIG. 1 is frontal view of the invention as applied to an injured individual.

Referring to FIG. 1, the junctional tourniquet A is shown having a strap 10 encircling an individual. The strap include an opening 12 having an upper portion 14 and lower portion 16. The opening allows the base plates to be slidably attached to eh strap while also allowing the shaft to extend through the strap.

A first base plate 18 can include a top member 20 (FIG. 4) and a bottom member 22 that sandwiches the top and bottom portion of the strap allowing the base place to slide along the top and bottom portion of the strap to position the base plate above the location on the individual where compression is desired. The ability to position the base plates along the strap allows the compressive force to be placed in the proper location based upon the body type and injury and injury location of the individual. In one embodiment, the top member and the bottom member of the base plate are secured through a plurality of screws.

Figure 4:
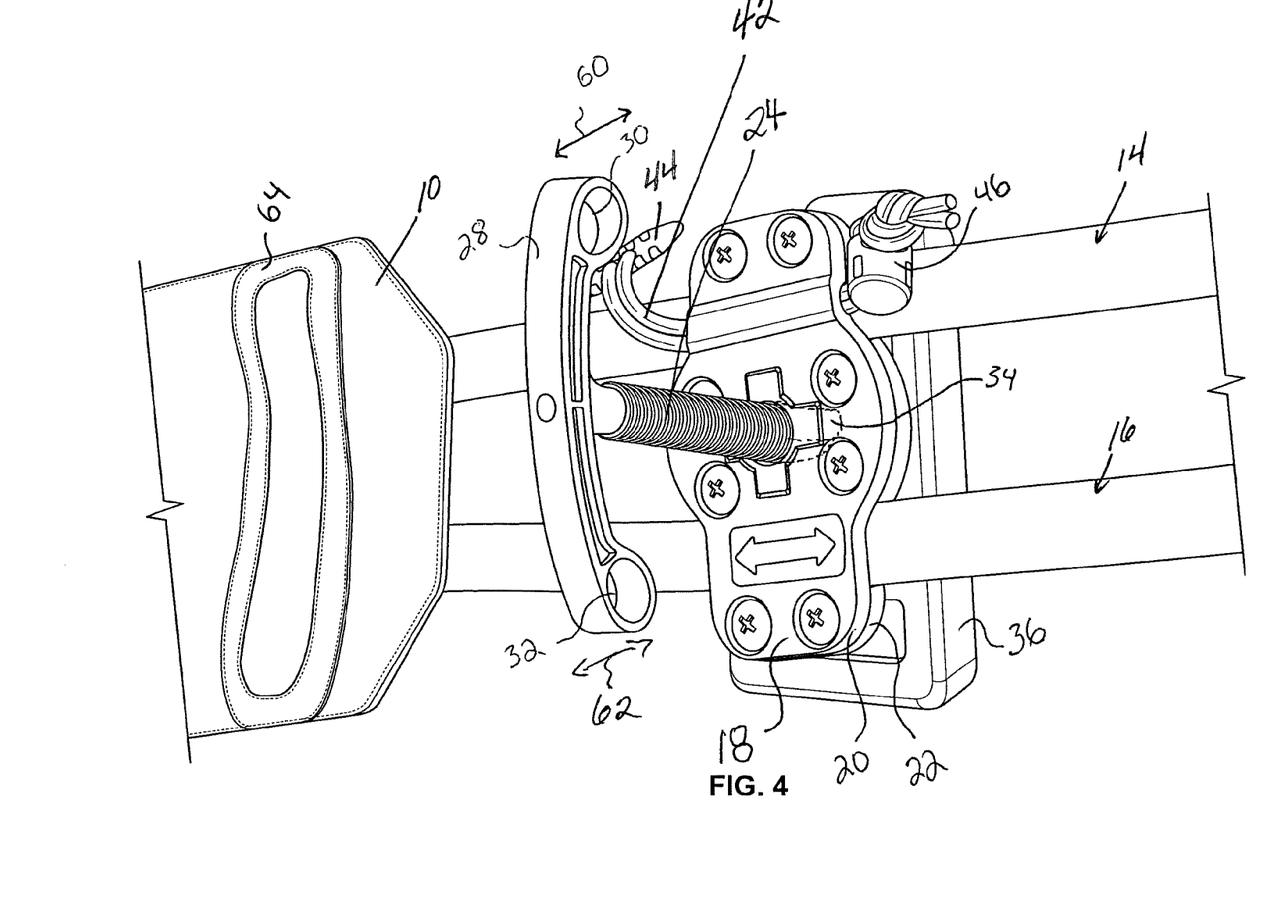
FIG. 4 is a perspective view of aspects of the invention.
Figure 5:
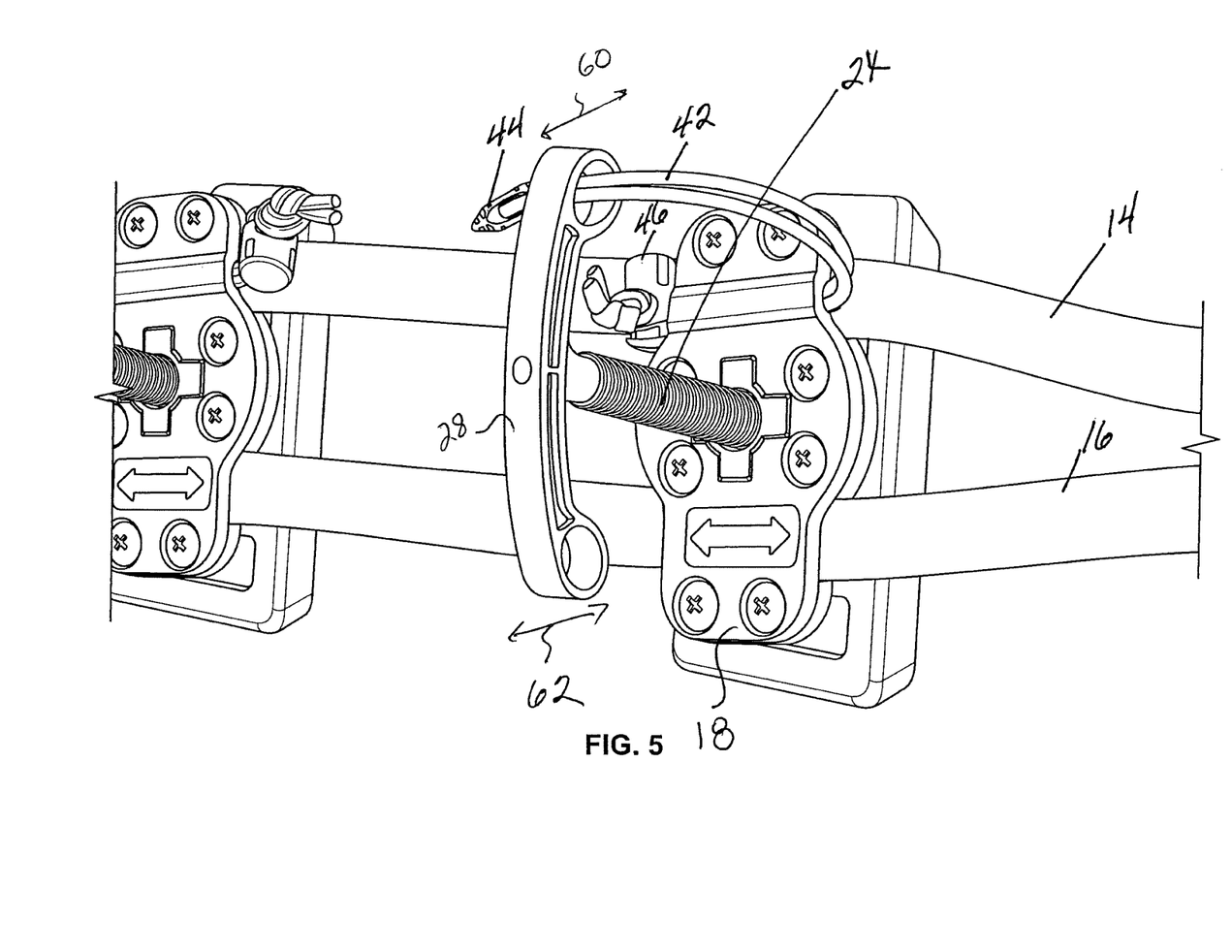
FIG. 5 is a perspective view of components of the invention.
Figure 6:
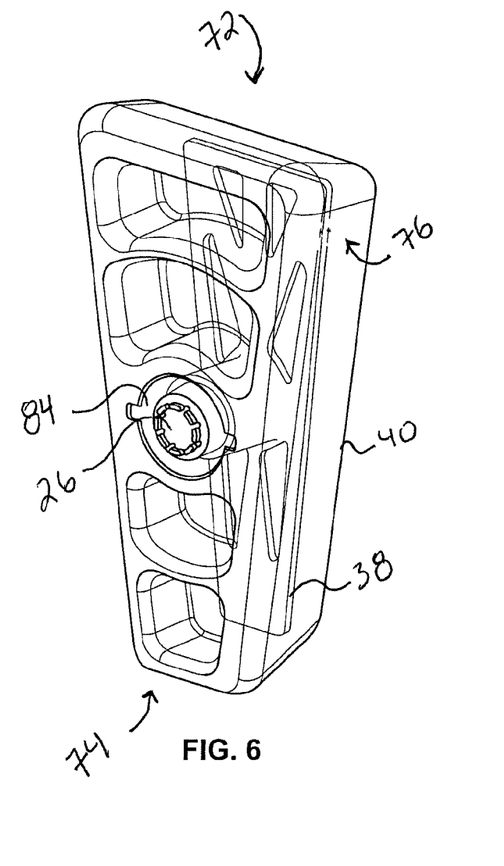
FIG. 6 is a perspective view of components of the invention.
Figure 7:
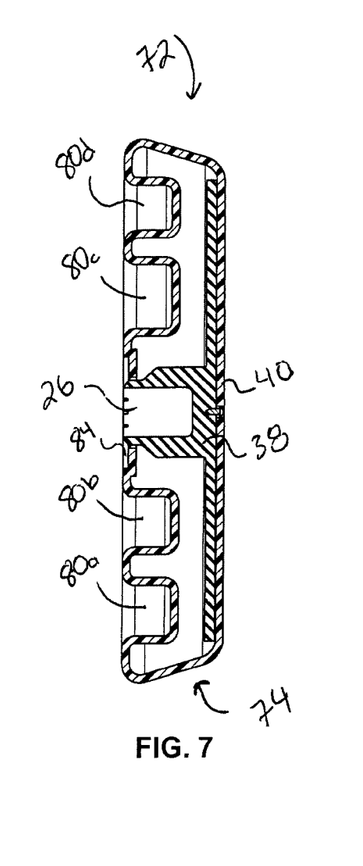
FIG. 7 is a cross section lengthwise of the pressure pad.
Figure 8:
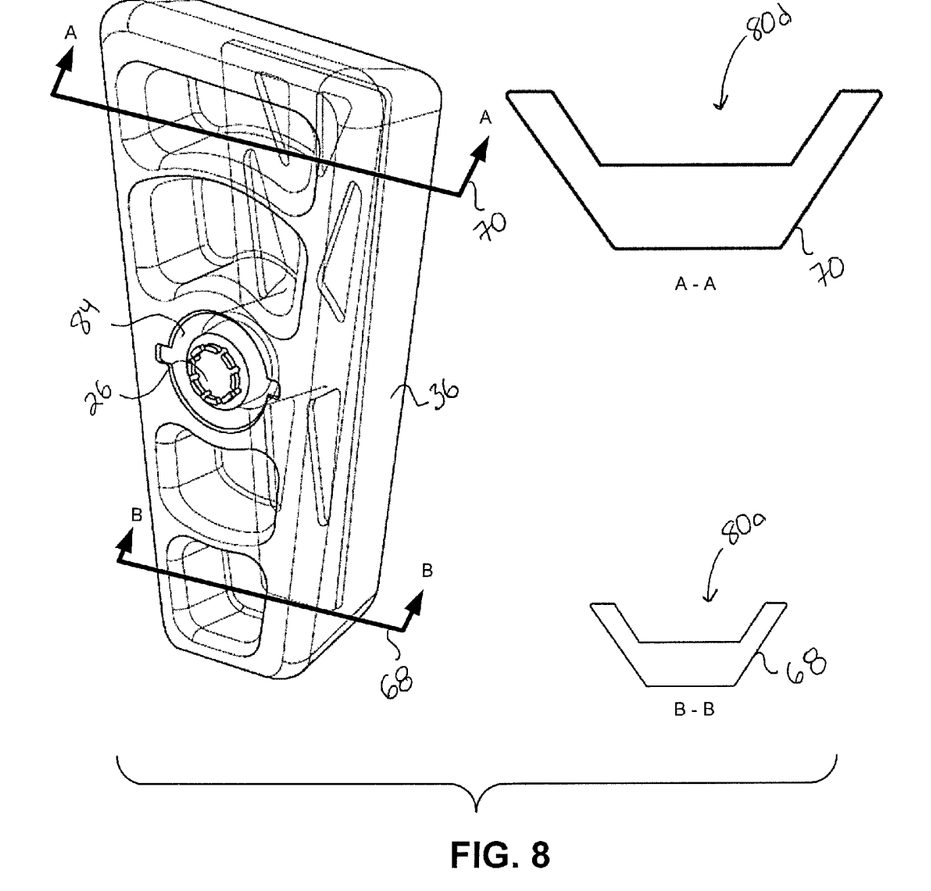
FIG. 8 is a perspective view and a cross section at one end width wise and a cross section width wise and the other end of the pressure pad.

A shaft 24 is received in a base plate opening 26 defined the base plate. In one embodiment, the shaft and base plate opening is threaded so that when the shaft rotated, the shaft extends into and retraces away from the base plate. A handle 28 is attached to a proximal end of the shaft and can include handle openings 30 and 32 at the ends of the handle. In one embodiment, the handle it a curved "T" handle configuration. The distal end can include a pressure fit member 34 for securing the shaft to a pressure pad 36. The pressure pad can include a core 38 that has an opening in the core for receiving the pressure fit member to secure the shaft to the pressure pad. The pressure pad can include a cross-section with a trapezoidal shape. In one embodiment, the cross-section 70 disposed at rear 72 of the pressure pad is of a larger area than the cross-section 68 disposed at front 74 of the pressure pad. In one embodiment, the rear end has a rear width and a front end has a front width wherein said front width and said rear width have a ratio of about 2:1. The side 76 of the pressure pad can have a side width wherein said ratio of said first end and said side width is about 2.25:1. In one embodiment, the pressure pad includes a contact surface 40 that has a surface area in the range of 35 cm² to 45 cm². In one embodiment, the area of the contact surface is 39 cm². In one embodiment, the contact surface has the dimensions 5 cm×10.6 cm×2.4 cm×10.6 cm. The non-contact side can have the dimensions 6 cm×11.7 cm×3.2 cm×11.7 cm. The distance between the contact surface and non-contact surface is 2.8 cm. The non-contact surface can include voids 80a through 80d to reduce material on the pressure pad to lighten the pad. In one embodiment the voids are contoured around the opening to receiving the shaft to increase strength in the pressure pad.

In one embodiment, the bottom portion of the base plate include a friction member which, when the pressure pad is forced against the base plate, engages the friction opening 84 further restricting the ability of the pressure pad to rotate in relation to the base plate.

The shaft can then be secured to the pressure pad while allowing the shaft to rotate independently of the pressure pad. When the handle rotates, the shaft extends toward the base plate thereby applying a compressive force to the individual through the pressure pad and a contact surface 40 included in the pressure pad that contacts the individual to restrict blood flow from an injured artery.

When the handle is turned in a first direction to apply compressive force, a rotational arresting strap 42 can be used to prevent the shaft from counter rotating. The rotational arresting strap can include a securing tab 44 attached to the rotational arresting strap that can be orientated so that its long axis 60 is aligned with the center axis 62 of the handle opening. When the securing tab is then orientated orthogonally to the center of the handle opening, the securing tab is prevented from withdrawing from the handle opening and due to the tension placed on the rotating arresting strap, prevents the handle from rotating. In one embodiment, the strap is slidably attached to the base plate. A slide lock 46 can be included on the strap so that when the strap is pulled through the base plate to place tension on the handle, the slide lock will secure the strap from releasing. In one embodiment, the strap is 550 paracord. In one embodiment, the slide lock is a cord tension lock.

Figure 2:
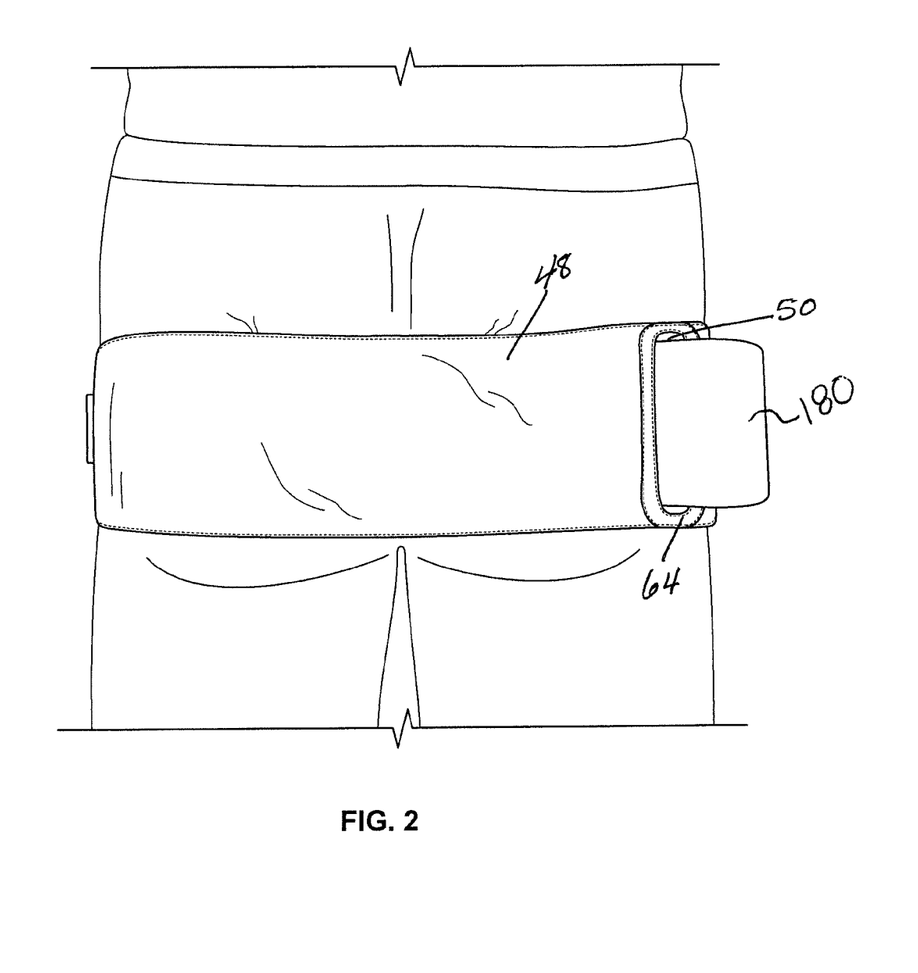
FIG. 2 is a rear view of the invention.
Figure 3:
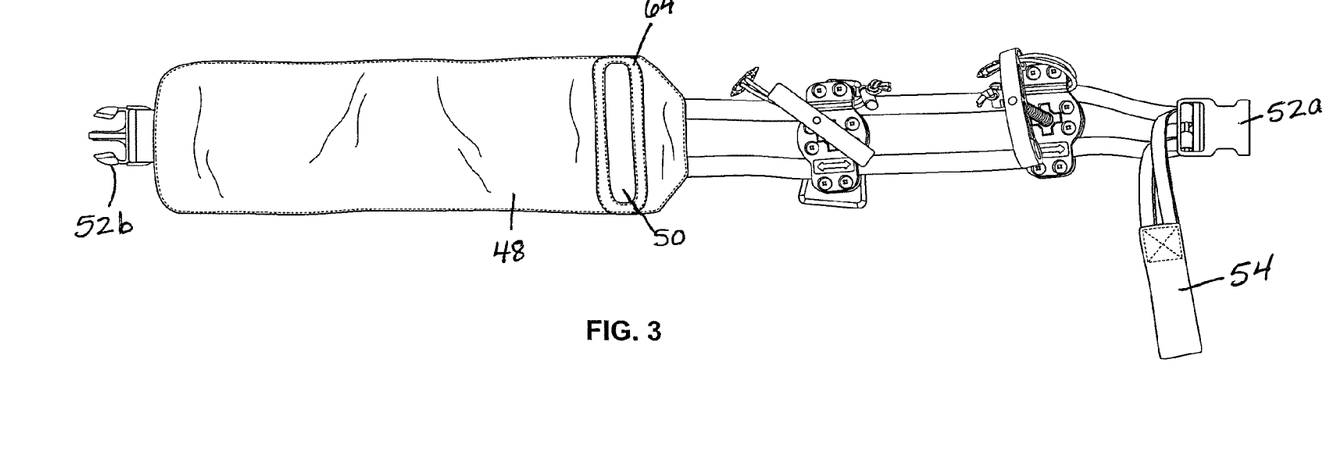
FIG. 3 is a top view of the invention.

In one embodiment, the strap includes a pelvic pad 48 that encircles the rear of the individual and when the strap is tightened. The pad can be a width greater than the rest of the strap. When applied, the pelvic pad can assist with applying a compressive force around the pelvic region to provide a pelvic binder. In one embodiment, the pelvic pad includes a pocket 50 defined in the pelvic pad. The pocket can receive a semi-rigid member 180 to add stability to the pelvic pad. In one embodiment, the SAM splint offered by SAM Medical Products, Inc. can be used as the semi-rigid stiffening member. The strap can be secured around the individual with a releasable fastener 52a and 52b. The strap can be tightened by end portion 54. In one embodiment, the opening of the pocket is highlighted with a contrasting indicator to more easily identify the insertion point for the semi-rigid stiffening member.

In operation, the strap is secured around the injured individual. The base plates are position in the junction of the leg and torso by sliding the base plates along the straps. The base plates are positioned based upon the body type of the injured individual, the type of injury and the location of the injury. The pressure pads are position so that the front of the pressure is pointed toward the legs of the individual and the pads are angled in the junction between the leg and the torso. The handles are rotated to force the contact surface of the pressure pad to apply compressive force to the individual. As the handles are rotatably attached to eh pressure pad, the pressure pad need not rotate when the handles are rotated. The rotating arresting strap tab is inserted into the handle opening. The tab is turn orthogonal to the handle opening preventing the tab from retracting through the opening. The rotating arresting strap is pulled to place tension on the rotational arresting strap. The slide is actuated to prevent the rotational arresting strap from extended from the base plate thereby arresting the rotation of the handle. In one embodiment, a semi-rigid stiffening member is placed in the pocket of the pelvic pad prior to applying the tourniquet to the individual.

While a preferred embodiment of the invention has been described using specific terms, such description is for illustrative purposes only, and it is to be understood that changes and variations may be made without departing from the spirit or scope of the following claims.

What is claimed is:

1. A tourniquet for use at junction points of an injured individual comprising:
    a strap for releasably encircling an injured individual;
    a pelvic pad included in said strap having a pocket defined in said pelvic pad for receiving a semi-rigid stiffening member;
    a plurality of base plates slidably attached to said strap allowing said base plates to be positioned along said strap at varying distances relative to each other;
    a shaft opening defined in each base plate having threads on an interior surface of said shaft openings;
    a threaded shaft received in each of said base plates;
    a pressure pad removably attached to a distal end of each of said shafts;
    a handle attached to a proximal end of each of said shafts having openings defined in each end of said handle; and,
    a rotational arresting strap attached to each base plate having a securing tab that can be received in one of said handle openings thereby preventing said shaft from rotating when said securing tab is received in said handle opening.

2. The tourniquet of claim 1, wherein said pressure pad includes a trapezoidal cross section.

3. The tourniquet of claim 2, where said pressure pad includes a trapezoidal cross section that reduces in area from a rear of said pressure pad to a front of said pressure pad.

4. The tourniquet of claim 1, wherein said pressure pad wherein a rear end has a rear width and a front end has a front width wherein said front width and said rear width have a ratio of about 2:1.

5. The tourniquet of claim 4, including a side having a side width wherein said ratio of said first end and said side width is about 2.25:1.

6. The tourniquet of claim 1, wherein said pressure pad includes a contact surface having an area of between 35 cm and 45 cm.

7. The tourniquet of claim 1, wherein each of said rotational arresting straps are slidably attached to said base plates so that said rotational arresting straps can be tensioned to arrest rotational movement of said shafts.

8. The tourniquet of claim 7, including a slide lock carried by each rotational arresting strap preventing said rotational arresting straps from losing tension.

9. The tourniquet of claim 1, including a friction member attached to a base plate for engaging a friction opening in said pressure pad further restriction the ability to of the pressure pad to rotate relative to said base plate.

10. The tourniquet of claim 1, wherein each of said pressure pads include a rigid core internal to said pressure pads having an opening for receiving said threaded shaft.

11. The tourniquet of claim 1, wherein each of said pressure pads are rotatably press fit to said threaded shafts allowing said pressure pads to rotate about said threaded shaft.

12. The tourniquet of claim 1, including a tightening buckle at the ends of said rotational arresting straps allowing said strap to be secured around the pelvic region of the injured individual placing tension on the pelvic region of said injured individual.

13. A tourniquet for use at junction points of an injured individual comprising:
    a strap for releasably encircling an injured individual;
    a base plate slidably attached to said strap allowing said base plate to be positioned along said strap;
    a shaft opening defined in said base plate;
    a threaded shaft received in said base plate;
    a pressure pad removable and rotatably attached to a distal end of said shaft;
    a handle attached to a proximal end of said shaft having an opening defined in said handle;
    a rotational arresting strap attached to said base plate having a securing tab that can be received into said handle opening thereby preventing said shaft from rotating when said securing tab is received in said handle opening;
    a pelvic pad included in said strap and configured to be generally disposed on the opposite side of the injured individual relative to the base plate when said strap is around said injured individual;
    a pocket defined in said pelvic pad; and,
    a semi-rigid stiffening member received in said pocket defined in said pelvic pad.

14. The tourniquet of claim 13, wherein said strap includes a slot defined in a portion of said strap for allowing the shaft to extend through the slot from one side of the strap to the other.

15. The tourniquet of claim 13, wherein the area of a cross section of said pressure pad decreases from a rear of said pressure pad to a front of said pressure pad.

16. A tourniquet for use at junction points of an injured individual comprising:
    a strap for releasably encircling an injured individual at the pelvic region;
    a pressure pad slidably carried by said strap attached to a threaded shaft having a handle so that when said handle is rotated, said pressure pad applies compressive force to the individual;
    a rotational arresting strap carried by said pressure pad having a securing tab that can be received in an opening defined in said handle thereby preventing said handle from rotating;
    a pocket defined in said strap wherein said pocket is configured to be disposed on an opposite side of the injured relative to the pressure pad when said strap is around said injured individual; and,
    a semi-rigid stiffening member received in said pocket configured to increase pelvic compressive force on the injured individual when said strap is tightened around said injured individual.

17. The tourniquet of claims 16, wherein a stiffening member includes a malleable metal core.

18. The tourniquet of claim 16, wherein said rotational arresting strap is 550 paracord and said 550 paracord can be secured from extending away from said base plate by a slide lock.

* * * * *